(12) United States Patent
Martz

(10) Patent No.: US 7,805,768 B2
(45) Date of Patent: Oct. 5, 2010

(54) LIQUID PENETRATION SHIELDS FOR OUTER GARMENTS

(76) Inventor: Christine Martz, 1128 Ruth Pl., North Bellmore, NY (US) 11710

( * ) Notice: Subject to any disclaimer, the term of this patent is extended or adjusted under 35 U.S.C. 154(b) by 220 days.

(21) Appl. No.: 11/447,215

(22) Filed: Jun. 5, 2006

(65) Prior Publication Data
US 2006/0230505 A1    Oct. 19, 2006

(51) Int. Cl.
A41D 27/12    (2006.01)
A41B 9/00     (2006.01)
A41B 9/02     (2006.01)
A61F 13/15    (2006.01)

(52) U.S. Cl. .................. 2/46; 2/400; 2/403; 604/387
(58) Field of Classification Search .......... 2/53–58, 2/46; 450/36, 37, 54–57; 604/385.07, 387, 604/391
See application file for complete search history.

(56) References Cited

U.S. PATENT DOCUMENTS

| | | | |
|---|---|---|---|
| 1,465,076 A | | 8/1923 | Dupont |
| 1,897,952 A | | 2/1933 | Dupont |
| 2,344,781 A | | 3/1944 | Mullen |
| 2,476,112 A | * | 7/1949 | Pinchoff ................ 2/231 |
| 2,534,934 A | | 12/1950 | Viniegra |
| 2,821,719 A | | 2/1958 | Meaker |
| 3,044,467 A | | 7/1962 | Campau |
| 3,077,603 A | | 2/1963 | Weaver |
| 3,315,677 A | * | 4/1967 | Tyrrell, Jr. ............. 604/396 |
| 3,339,208 A | | 9/1967 | Marbach |
| 3,397,697 A | * | 8/1968 | Rickard ................ 604/370 |
| 3,997,920 A | * | 12/1976 | DeWoskin ................ 2/53 |
| 4,227,264 A | | 10/1980 | Spector |
| 4,244,368 A | | 1/1981 | Caradonna |
| 4,333,466 A | | 6/1982 | Matthews |

(Continued)

FOREIGN PATENT DOCUMENTS

CA    2285646 A1    4/2001

(Continued)

OTHER PUBLICATIONS

Frankel; Julie Robin Faxed Declaration dated Sep. 10, 2004, and Trademark registration file for anti-panti, reg. No. 2,962,300, 19 pages.

(Continued)

Primary Examiner—Gary L Welch
Assistant Examiner—Amber R Anderson
(74) Attorney, Agent, or Firm—Alfred M. Walker

(57) ABSTRACT

A shield protects an outer garment, such as a pair of pants, against visible staining caused by a small amount of liquid, such as urine or lactating milk. The shield includes a multiple layer laminate constructed of an absorptive layer, a soft plastic barrier layer adjoined on one side to said absorptive layer, and a gripping layer on an opposite side of said soft plastic layer adapted to mechanically lock and adhere onto the outer garment. The shield is placed into the zipper fly or crotch area of any male or female pant garment, or inside of a blouse of a lactating woman. The shield provides a healthy safe barrier between the individual and the garment. It remains securely in place and feels cool and comfortable and can be changed easily when needed.

9 Claims, 3 Drawing Sheets

U.S. PATENT DOCUMENTS

| | | | |
|---|---|---|---|
| 4,347,092 A | | 8/1982 | Hlaban et al. |
| 4,425,130 A | | 1/1984 | DesMarais |
| 4,518,451 A | | 5/1985 | Luceri et al. |
| 4,545,080 A | * | 10/1985 | Gorham .................. 2/54 |
| 4,601,716 A | | 7/1986 | Smith |
| 4,605,404 A | | 8/1986 | Sneider |
| 4,648,876 A | | 3/1987 | Becker et al. |
| 4,653,119 A | * | 3/1987 | Kaiser .................. 2/60 |
| 4,738,676 A | | 4/1988 | Osborn, III |
| 4,747,162 A | | 5/1988 | Yanagihara |
| 4,834,739 A | | 5/1989 | Linker, III et al. |
| 4,846,829 A | | 7/1989 | Lloyd |
| 4,847,134 A | | 7/1989 | Fahrenkrug |
| 4,882,220 A | | 11/1989 | Ono et al. |
| 4,905,323 A | | 3/1990 | Lampman |
| 4,917,920 A | | 4/1990 | Ono et al. |
| 4,951,321 A | | 8/1990 | Mortenen et al. |
| 4,955,088 A | | 9/1990 | Terjesen |
| 4,955,880 A | | 9/1990 | Rodriguez |
| 4,961,234 A | | 10/1990 | Leibman |
| 4,982,450 A | | 1/1991 | D'Hussier |
| 5,010,595 A | | 4/1991 | Stradley |
| 5,042,088 A | * | 8/1991 | Sherrod et al. .................. 2/53 |
| 5,072,454 A | | 12/1991 | Trahan |
| 5,081,718 A | | 1/1992 | Carman |
| 5,095,549 A | | 3/1992 | Aldridge |
| 5,103,501 A | | 4/1992 | Meisels |
| 5,242,632 A | | 9/1993 | Mende |
| 5,308,695 A | * | 5/1994 | Arakawa et al. ............. 428/354 |
| 5,342,332 A | | 8/1994 | Wheeler |
| 5,344,698 A | | 9/1994 | Rock |
| 5,347,657 A | | 9/1994 | Unsell |
| 5,367,715 A | | 11/1994 | Leonard |
| 5,370,632 A | | 12/1994 | Beplate |
| 5,388,275 A | | 2/1995 | Oram |
| 5,415,650 A | | 5/1995 | Sigl |
| 5,467,482 A | | 11/1995 | Crawford |
| 5,531,725 A | | 7/1996 | Steer |
| 5,570,471 A | * | 11/1996 | Krawchuk .................. 2/53 |
| 5,591,146 A | | 1/1997 | Hasse |
| 5,593,398 A | | 1/1997 | Weimer |
| H1639 H | | 3/1997 | Crainic |
| 5,611,790 A | | 3/1997 | Osborn, III et al. |
| 5,678,251 A | | 10/1997 | Getz |
| 5,729,835 A | | 3/1998 | Williams |
| 5,774,891 A | | 7/1998 | Boyer |
| 5,778,457 A | | 7/1998 | Conway |
| 5,807,365 A | | 9/1998 | Luceri |
| 5,832,535 A | | 11/1998 | Davis |
| D405,938 S | | 2/1999 | Trombetta |
| 5,884,330 A | | 3/1999 | Erlich |
| 5,903,922 A | | 5/1999 | Vargason |
| 5,946,730 A | | 9/1999 | Blair |
| 6,000,056 A | | 12/1999 | Brady et al. |
| 6,049,915 A | | 4/2000 | Malowaniec |
| 6,049,916 A | | 4/2000 | Rajala et al. |
| 6,067,663 A | | 5/2000 | Fernandez |
| 6,093,178 A | | 7/2000 | Osborn, III et al. |
| 6,098,203 A | | 8/2000 | Rajala et al. |
| D434,145 S | | 11/2000 | Sugahara |
| 6,162,457 A | | 12/2000 | Martz |
| 6,162,961 A | | 12/2000 | Tanner |
| 6,173,449 B1 | | 1/2001 | Osterrath |
| 6,176,850 B1 | | 1/2001 | Rosenfeld et al. |
| 6,210,386 B1 | | 4/2001 | Inoue |
| 6,219,846 B1 | | 4/2001 | Toole |
| 6,231,558 B1 | | 5/2001 | Mosley |
| 6,232,250 B1 | | 5/2001 | Palumbo |
| D443,358 S | | 6/2001 | Jonsdottir |
| 6,240,569 B1 | | 6/2001 | Van Gompel et al. |
| 6,247,184 B1 | | 6/2001 | Watts |
| D444,554 S | | 7/2001 | O'Hara |
| 6,260,211 B1 | | 7/2001 | Rajala et al. |
| 6,269,486 B1 | * | 8/2001 | Nager et al. .................. 2/53 |
| 6,277,223 B1 | | 8/2001 | Herrin et al. |
| 6,306,122 B1 | | 10/2001 | Narawa et al. |
| 6,307,120 B1 | | 10/2001 | Glaug |
| 6,313,371 B1 | | 11/2001 | Conant et al. |
| 6,315,022 B1 | | 11/2001 | Herrin et al. |
| 6,317,893 B1 | | 11/2001 | Walton |
| 6,364,863 B1 | | 4/2002 | Yamsmoto et al. |
| 6,367,089 B2 | | 4/2002 | Van Gompel et al. |
| 6,371,831 B1 | | 4/2002 | Dodge |
| 6,391,011 B1 | | 5/2002 | Davis et al. |
| 6,392,117 B1 | | 5/2002 | Mayer et al. |
| 6,401,250 B1 | | 6/2002 | McNabb |
| 6,406,462 B1 | | 6/2002 | Johnson |
| 6,409,712 B1 | | 6/2002 | Dutari |
| 6,490,732 B1 | | 12/2002 | Spoke |
| 6,497,688 B2 | | 12/2002 | Lasko |
| 6,681,407 B2 | | 1/2004 | Martz |
| 6,903,243 B1 | * | 6/2005 | Burton .................. 602/41 |
| 2001/0044964 A1 | * | 11/2001 | Phillips .................. 5/485 |
| 2002/0184698 A1 | | 12/2002 | Harris |
| 2003/0019251 A1 | | 1/2003 | Browder |
| 2003/0028162 A1 | | 2/2003 | Haarer |
| 2003/0167550 A1 | * | 9/2003 | Andrews .................. 2/53 |
| 2003/0221236 A1 | * | 12/2003 | Hippensteel .................. 2/46 |
| 2004/0068247 A1 | | 4/2004 | Connor |
| 2004/0117895 A1 | | 6/2004 | Fortner |

FOREIGN PATENT DOCUMENTS

| | | |
|---|---|---|
| CH | 613101 A5 | 9/1979 |
| WO | 9416655 A2 | 8/1994 |
| WO | 0025726 A2 | 5/2000 |
| WO | WO 01/49232 A | 7/2001 |

OTHER PUBLICATIONS

Frankel; Julie Robin, website: "antipanti.com", copyright 2004, 5 pages.

True Fit Try On garment liners, Internet page, www.truefittryon.com, 3 pages, showing liners.

* cited by examiner

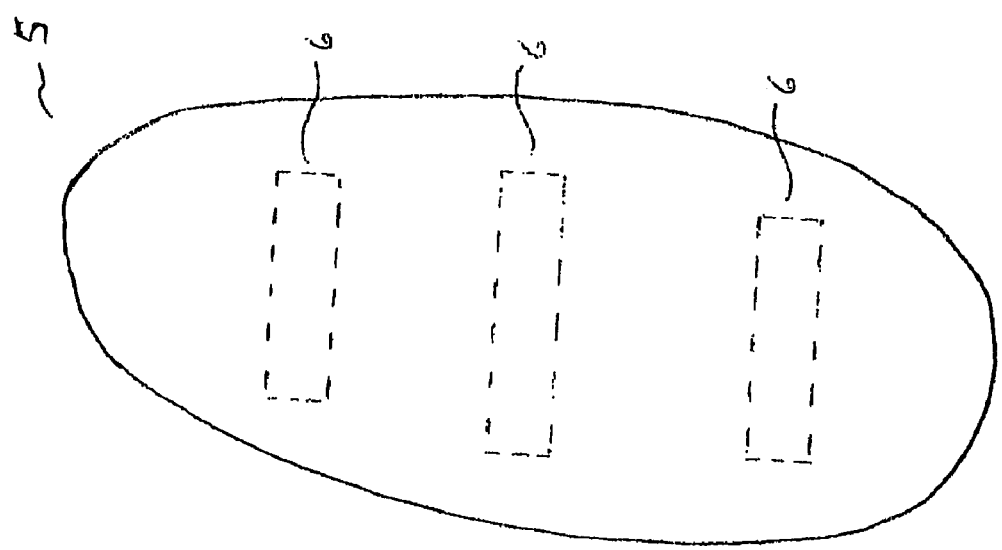
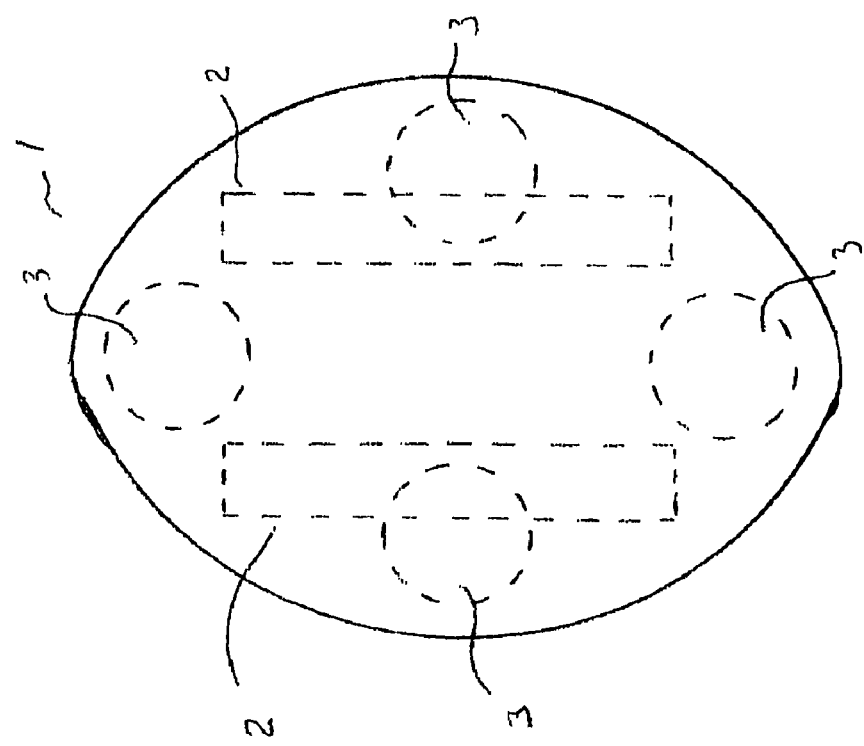

LIQUID PENETRATION SHIELDS FOR OUTER GARMENTS

CROSS REFERENCE TO RELATED APPLICATIONS

This application discloses in part, and claims priority under 35 U.S.C. 120, subject matter disclosed in my earlier U.S. patent applications filed under Ser. No. 10/741,176, of Dec. 20, 2003 and Ser. No. 10/202,350 of Jul. 24, 2002, now U.S. Pat. No. 6,681,407 dated Jan. 27, 2004, which are hereby incorporated by reference. This application also claims benefit under 35 U.S.C. 119(e) from provisional application No. 60/390,939 of Jun. 24, 2002.

FIELD OF THE INVENTION

The present invention relates to liquid penetration shields for outer garments, to avoid visible urinary staining of outer garments.

BACKGROUND OF THE INVENTION

Urinary incontinence affects 13 million people in the U.S. Regardless of age, young or old alike, incontinence causes great embarrassment and distress. For example, in children about 20% of 5-year-old's are affected. They experience urine leakage for a variety of reasons such as overactive bladder, anxiety, small bladders that fill quickly, developmental delays, urinary track infections, or just being engrossed in an activity. For whatever reason, the slightest leakage causes the dreaded visible stain.

OBJECTS OF THE INVENTION

It is therefore an object of the present invention to provide a liquid penetration shield for an outer garment, such as pants, which avoids visible urinary staining of through the outer garment.

SUMMARY OF THE INVENTION

The liquid penetration shield of this invention, known as the No Show Guard™, provides an extra barrier to prevent a small amount of urine or other bodily fluids from penetrating through the outer garment possibly causing embarrassment and anxiety due to the visible stain. Due to its wicking action, the liquid penetration shield may promote healing of rashes or sensitive areas; it can also reduce offensive odor. The liquid penetration shield may be used as a hygienic alternative to underwear, and it is available in a variety of sizes, shapes, colors and prints.

For the female user, it is to be worn on the inner crotch area of a pant garment. It can be placed horizontally or vertically. For the male user it is best placed from the center crotch extending upward on either side of the fly zipper. In doing so, any urine spots that would result from leakage will go directly onto the liquid penetration shield instead and will not penetrate the garment, thereby preventing a visible stain.

Other feminine uses of the liquid penetration shield are noted. If a woman chooses to add more protection during menstruation or while using tampons, she is assured that the protection from the guard which has a light plastic layer within will keep her dry and confident. A nursing woman also benefits from the Liquid penetration shield. It can easily be inserted into her bra for added protection or positioned on the inside of her blouse so that any lactating fluid which might penetrate will not become visible and stain garments.

The material of a liquid penetration shield is generally less than 1 mm (0.039") thick, although added fluid retention (if desired) can be achieved with a thicker absorptive layer. The material is constructed as a three layer laminate, with a soft absorptive layer on top, a soft plastic barrier layer next, and a bottom layer which mechanically locks onto soft fabrics such as flannel when pressed against it. An example of the bottom layer is a diaper tab that is sometimes used on disposable diapers; it is a substrate with hook-like protrusions on one surface which behave like the hook material of VELCRO® hook and loop fasteners, only less than ¼ of the typical VELCRO® thickness. Since the bottom layer does not mate aggressively to types of fabrics such as denim, the user can use strips of double-sticky tape to attach the liquid penetration shield.

Alternatively, the bottom layer of the shield can be an adhesive layer with a pull off release liner, wherein the adhesive layer attaches directly to the inside of the outer garment fabric material, rather than to a base.

However, it is preferable to alter the crotch (and inner fly areas for male use) of pants with the addition of soft fabric material to facilitate the simple non-adhesive press-on application. This would eliminate any adhesive debris on the garment. In an alternate embodiment, the bottom layer of the liquid penetration shield is eliminated and small patches of the mechanically attachable material are factory-attached to the plastic barrier layer instead. This significantly reduces the thickness (except in the areas of the attachment patches) and permits a more flexible liquid penetration shield.

BRIEF DESCRIPTION OF THE DRAWINGS

The present invention can best be understood in connection with the accompanying drawings. It is noted that the invention is not limited to the precise embodiments shown in drawings, in which:

FIG. 1 is a top plan view of a liquid penetration shield of this invention showing the placement of optional tape attachment strips;

FIG. 2 is a top plan view of an alternative shape of a liquid penetration shield showing placement of optional tape attachment strips;

DETAILED DESCRIPTION OF THE INVENTION

Figure 4:
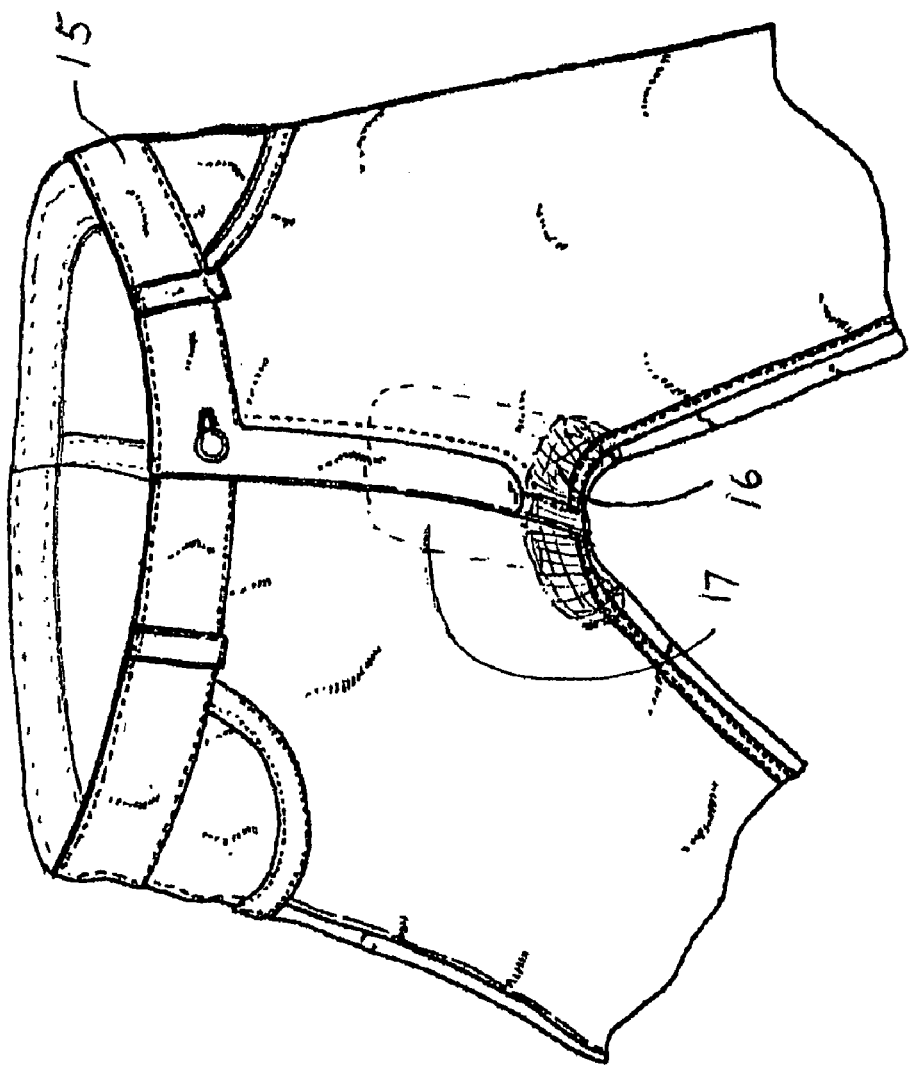
FIG. 4 is a perspective detail of a pants illustrating the areas protected by the liquid penetration shield.

FIGS. 1 and 2 show two different shapes of the liquid penetration shield for outer garments, such as pants.

In FIG. 1, guard 1 is a modified oval shape for feminine use in the crotch area of pants. Rectangular dashed outlines 2 and circular outlines 3 illustrate the placement of optional adhesive strips for attachment to material which does not mate with the mechanical fastener bottom layer.

In FIG. 2, guard 5 is more elongated, and optional adhesive strips 6 are short and orthogonal to those in FIG. 1.

Figure 3:
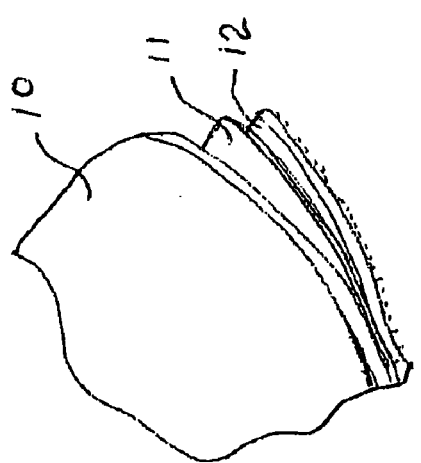
FIG. 3 is a perspective detail view of the material of the liquid penetration shield showing the three layers of the laminate forming the liquid penetration shield.

FIG. 3 shows the construction of the three layer laminate of the liquid penetration shield. Top layer 10 is a soft absorptive layer. Although guards can be washable and reusable, the disposable version is most hygienic and convenient. For a disposable guard, top layer 10 can be as thin as 0.006" (0.15 mm) of a paper material such as is used on a disposable baby bib. A thicker layer 10 would have a higher absorption capacity however. The next layer, 11, is the barrier layer which can be from 0.5-1.0 mil (0.013-0.026 mm). The bottom layer, 12, is the "hook" material similar to that on diaper tabs. This material is approximately 0.024" (0.61 mm) thick including "hooks" which protrude from the bottom surface about 0.016" (0.4 mm). By eliminating layer 12 and using patches of hook material instead (see items 3 in FIG. 1) the liquid penetration shield can be substantially thinner and far more pliable, but in any case, even with layer 12 the total thickness is less than 1 mm.

FIG. 4 shows a pants detail with belt 15 highlighting the region 16 that is protected by a feminine liquid penetration shield. The added region 17 shown by the dashed lines is the additional area of the pants protected by a male liquid penetration shield. The inside of the pants in these regions can be modified by the addition of soft fabric to facilitate the non-adhesive attachment of liquid penetration shields by just pressing the bottom layer (or attachment patch areas) into the soft fabric.

Figure 5:
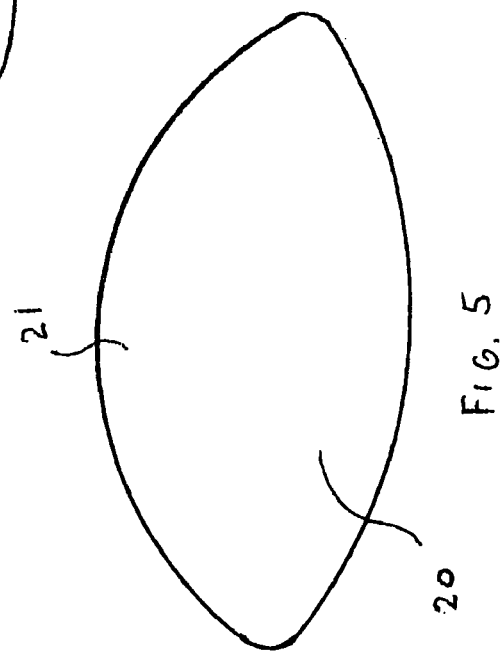
FIG. 5 is a top plan view of the liquid penetration shield for young girls offering more frontal protection.

FIG. 5 shows the liquid penetration shield 20 shape with elongated front section 21 for higher front pant protection for younger girls.

Figure 7:
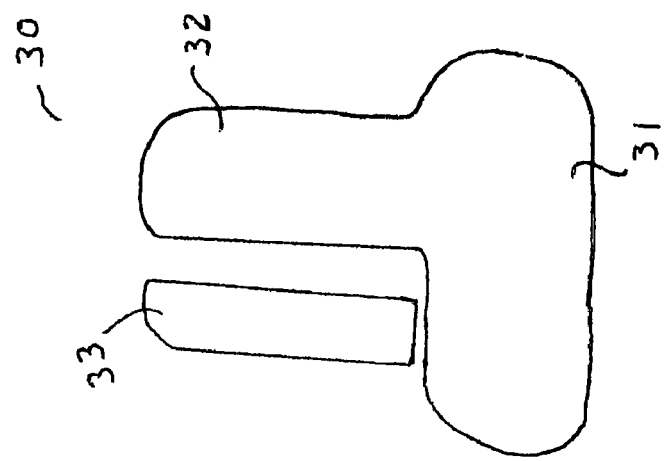
FIG. 7 is a top plan view of an alternate embodiment of a liquid penetration shield for male use with a separate front guard strip; and, FIG. 8 is a top plan view for a further alternate embodiment for a liquid penetration shield for male use made up of a pair of strip pads.
Figure 6:
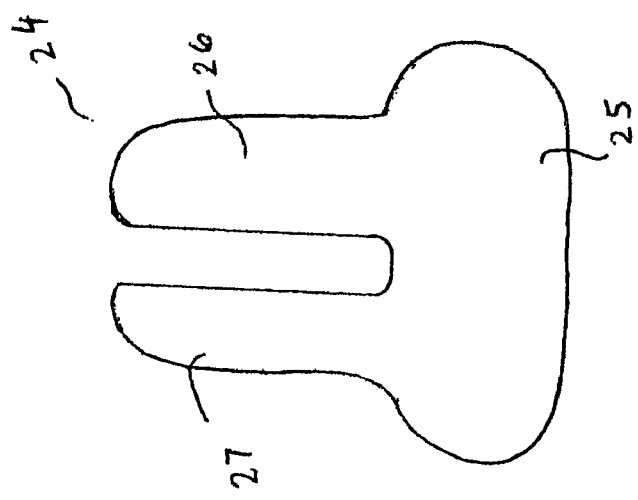
FIG. 6 is a top plan view of the liquid penetration shield for male use with attached frontal features.

FIGS. 6 and 7 show two different embodiments of the liquid penetration shields for male use. FIG. 6 is a one-piece guard 24 with base 25 which covers the crotch area, and two fold-up extensions 27 and 26. Wide section 26 attaches behind the zipper on the fabric of the fly. The narrow section is attached adjacent to the side of the fly fabric on the pants front. The gap section has two double layers of fly fabric and is unlikely to show any penetration staining.

Guard 30 shown in FIG. 7 is a two-piece embodiment with a separate strip 33 to protect one front area adjacent to one side of the fly. Section 32 attaches to the back of the fly strip behind the zipper, and 31 covers the crotch area.

Figure 8:
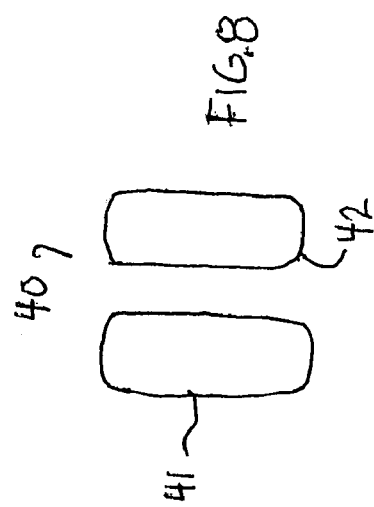

Alternatively, as shown in FIG. 8, especially for young boys who may intermittently dribble small amounts of urine through the front of a pair of pants, a pair 40 of oblong or other lengthwise extending pads 41 and 42 may be placed on the left and right sides respectively of a zipper fly.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

I claim:

1. A shield for protecting an outer garment against visible staining caused by a small amount of liquid comprising a multiple layer laminate constructed of an absorptive layer, a soft plastic barrier layer adjoined on one side to said absorptive layer, and a gripping layer on an opposite side of said soft plastic barrier layer adapted to mechanically lock releasably and detachably directly onto said outer garment without use of an adhesive or stitching in which said shield is a generally U-shaped shield of two piece construction with an L-shaped portion of said U-shaped shield having one leg parallel and adjacent to one side of said fly and a straight portion of said U-shaped shield on an opposite side of and adjacent to said fly, with a second leg of said L-shaped portion of said U-shaped shield being adjacent to a bottom end of said fly, said L-shaped portion and said straight portion forming a U-shape.

2. The shield of claim 1 in which said gripping layer comprises a substrate with hook-like protrusions for attaching to said outer garment.

3. The shield of claim 2 in which the substrate of said gripping layer is about 0.4 mm. in thickness and the gripping layer is a total of 0.61 mm. in thickness including said hook-like protrusions.

4. The shield of claim 1 in which said gripping layer comprises a plurality of patches each made up of a substrate with hook-like protrusions for reducing thickness of the shield in selected areas.

5. The shield of claim 1 in which said shield is disposable, said absorptive layer being about 0.15 mm. in thickness.

6. The shield of claim 5 in which said absorptive layer is a paper material.

7. The shield of claim 1 in which said barrier layer which has a thickness in the range of 0.013 to 0.026 mm.

8. The shield of claim 1 in which said liquid is a body fluid.

9. The shield of claim 8 in which said body fluid is urine.

* * * * *